United States Patent
Li et al.

(10) Patent No.: US 10,744,715 B2
(45) Date of Patent: Aug. 18, 2020

(54) BIOPRINTER SPRAY HEAD ASSEMBLY AND BIOPRINTER

(71) Applicant: REVOTEK CO., LTD, Chengdu, Sichuan (CN)

(72) Inventors: Yijun Li, Chengdu (CN); Deming Wang, Chengdu (CN); Leqing Zhang, Chengdu (CN); Xuemin Wen, Chingdu (CN)

(73) Assignee: Revotek Co., Ltd, Chengdu, Sichuan (CN)

( * ) Notice: Subject to any disclaimer, the term of this patent is extended or adjusted under 35 U.S.C. 154(b) by 10 days.

(21) Appl. No.: 16/067,566

(22) PCT Filed: Dec. 30, 2015

(86) PCT No.: PCT/CN2015/099855
§ 371 (c)(1),
(2) Date: Jun. 29, 2018

(87) PCT Pub. No.: WO2017/113186
PCT Pub. Date: Jul. 6, 2017

(65) Prior Publication Data
US 2019/0009467 A1    Jan. 10, 2019

(51) Int. Cl.
*B29C 64/20* (2017.01)
*B29C 64/209* (2017.01)
(Continued)

(52) U.S. Cl.
CPC .............. *B29C 64/209* (2017.08); *A61F 2/02* (2013.01); *B05B 7/0408* (2013.01); *B33Y 30/00* (2014.12);
(Continued)

(58) Field of Classification Search
CPC ..... B29C 64/209; B29C 64/106; B33Y 40/00; B33Y 30/00; B05B 7/0408; B05B 7/0012;
(Continued)

(56) References Cited

U.S. PATENT DOCUMENTS

| 5,074,443 A | 12/1991 | Fujii et al. |
| 6,267,266 B1 | 7/2001 | Smith et al. |
| 2007/0063400 A1 | 3/2007 | Yamaguchi et al. |

FOREIGN PATENT DOCUMENTS

| CN | 103009812 A | 4/2013 |
| CN | 203665960 U | 6/2014 |

(Continued)

OTHER PUBLICATIONS

Japanese Office Action dated Dec. 3, 2019 in connection with JP Patent Application No. 2018-534119.
(Continued)

*Primary Examiner* — Joseph S Del Sole
*Assistant Examiner* — Jamel M Nelson
(74) *Attorney, Agent, or Firm* — Wolf, Greenfield & Sacks, P.C.

(57) ABSTRACT

The present disclosure relates to a bioprinter spray head assembly and a bioprinter, wherein the bioprinter spray head assembly comprises a spray head and an extension rod spaced from the spray head and disposed adjacent to an outlet of the spray head, wherein an elongated flow channel is provided in the extension rod to guide a fluid printing unit serving as a biological printing material in the flow channel to be orientedly sprayed. The bioprinter spray head assembly
(Continued)

is configured such that a fluid print unit serving as a biological printing material is orientedly sprayed through the flow channel by providing an extension rod having an elongated flow channel adjacent to the outlet of the spray head. The elongated flow channel can perform an oriented sequence of the fluid printing unit, so as to reduce the possibility of clogging.

13 Claims, 1 Drawing Sheet

(51) Int. Cl.
| | | |
|---|---|---|
| *B33Y 30/00* | (2015.01) | |
| *A61F 2/02* | (2006.01) | |
| *B05B 7/04* | (2006.01) | |
| *B33Y 40/00* | (2020.01) | |
| *A61F 2/30* | (2006.01) | |
| *B05B 7/00* | (2006.01) | |
| *B41J 2/14* | (2006.01) | |
| *B29C 64/106* | (2017.01) | |

(52) U.S. Cl.
CPC ..... *B33Y 40/00* (2014.12); *A61F 2002/30985* (2013.01); *B05B 7/0012* (2013.01); *B29C 64/106* (2017.08); *B41J 2/1433* (2013.01); *B41J 2002/14475* (2013.01)

(58) Field of Classification Search
CPC . A61F 2/02; B41J 2/1433; B41J 2002/14475; B41J 2002/30985
See application file for complete search history.

(56) References Cited

FOREIGN PATENT DOCUMENTS

| | | |
|---|---|---|
| CN | 203994731 U | 12/2014 |
| CN | 104441654 A | 3/2015 |
| CN | 204382664 U | 6/2015 |
| CN | 104742366 A | 7/2015 |
| CN | 105167879 A | 12/2015 |
| CN | 204894532 U | 12/2015 |
| CN | 105167879 B * | 8/2017 |
| EP | 0056735 A2 | 7/1982 |
| WO | WO 2014/194180 A1 | 12/2014 |

OTHER PUBLICATIONS

PCT/CN2015/099855, Sep. 21, 2016, International Search Report and Written Opinion.
International Search Report and Written Opinion for PCT/CN2015/099855, dated Sep. 21, 2016.
Extended European Search Report and Search Opinion for EP 15911815.7, dated Jul. 3, 2019.

* cited by examiner

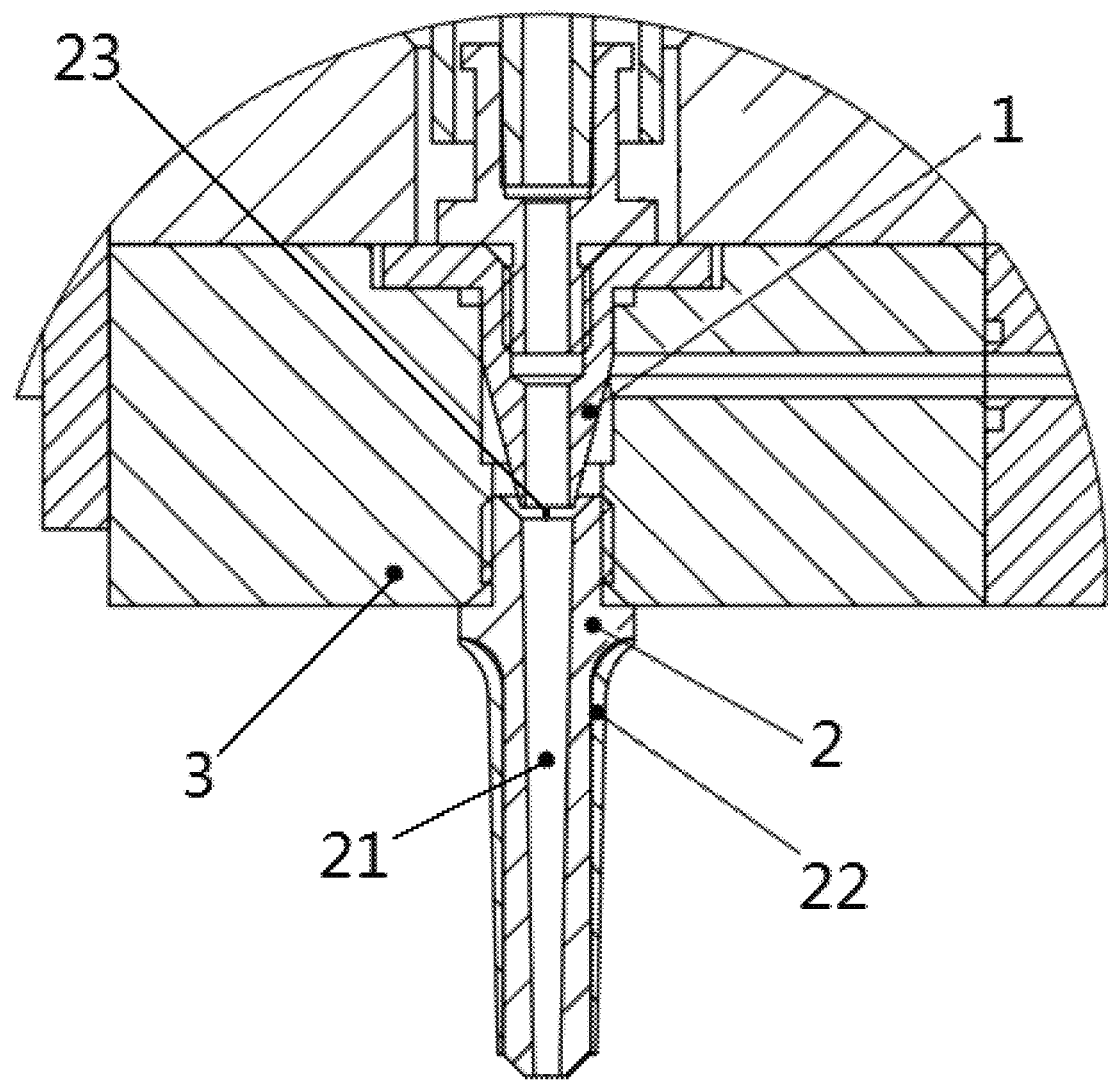

BIOPRINTER SPRAY HEAD ASSEMBLY AND BIOPRINTER

RELATED APPLICATIONS

This application is a national stage filing under 35 U.S.C. § 371 of International Patent Application Serial No. PCT/CN2015/099855, filed Dec. 30, 2015, the content of which is incorporated herein by reference in its entirety.

TECHNICAL FIELD

The present disclosure relates to the field of bioprinting, and especially relates to a bioprinter spray head assembly and a bioprinter.

BACKGROUND ART 3D bioprinting refers to the printing of biological materials (including natural biological materials and synthetic biological materials or cellular solutions) into a designed three-dimensional structure through the principles and methods of 3D printing. Differing from those printed by ordinary 3D printing technology, the biological tissues or organs produced by 3D bioprinting technology have certain biological functions and need to provide conditions for the further growth of cells and tissues. Exactly due to the aforementioned characteristics, the 3D bioprinting technology is confronted with many specific technical problems in development.

In the field of 3D bioprinting, the print technique of taking cells as a printing material is referred to as cell three-dimensional printing technology. People may utilize cells and biocompatible materials to make bio-ink. The spray head moves and sprays the bio-ink, and the movement of the spray head is controlled by a program to print the bio-ink. The bio-ink is printed and molded according to a three-dimensionally constructed digital model of a preset target print object.

The disadvantages of the prior art lie in that:

1. The bio-ink made from a biocompatible material has a high viscosity and a comparatively poor fluidity. It is prone to the problem of clogging near the spray head during the printing, which affects the printing efficiency.

2. In such process that the existing 3D bioprinting device directly sprays the cells to the printing platform at the spray head, due to the influence of the mechanical force in the printing process, the cells in the bio-ink may be significantly damaged, and the survival rate of the cells is difficult to guarantee, so as to affect the construction of a biological construct.

CONTENT OF THE DISCLOSURE

In order to overcome the above technical defects, the technical problem solved by the present disclosure is to provide a bioprinter spray head assembly and a bioprinter, which are capable of preventing clogging of the biological printing material.

To solve the aforementioned technical problem, the present disclosure provides a bioprinter spray head assembly, which comprises a spray head and an extension rod spaced from the spray head and disposed adjacent to an outlet of the spray head, wherein an elongated flow channel is provided in the extension rod to guide a fluid printing unit serving as a biological printing material in the flow channel to be orientedly sprayed.

In the basic technical solution, a fluid print unit serving as a biological printing material is orientedly sprayed through the flow channel by providing an extension rod having an elongated flow channel adjacent to the outlet of the spray head. The flow channel can perform an oriented sequence of the fluid printing unit, so as to reduce the possibility of clogging.

Further, the flow channel is tapered from its inlet to outlet.

In the improved technical solution, the flow channel is designed in a structural form tapered from its inlet to outlet. The fluid printing unit travels progressively in the flow channel, which facilitates raising the flow velocity of the fluid printing unit at the outlet of the flow channel, and further reducing the possibility of its clogging.

Further, the flow channel has a conical section taken along a flow direction of the fluid printing unit.

In the improved technical solution, the flow channel is further designed in a conical structural form, which makes a more uniform distribution of the fluid printing unit in the flow channel, and further reduces the possibility of its clogging. Moreover, the conical flow channel is easy to process.

Further, the outlet of the flow channel is sized to be 1-1.5 times the size of the fluid printing unit. Preferably, the outlet of the flow channel is sized to be 1.2 times the size of the fluid printing unit.

In the improved technical solution, it is only possible to flow out a single row of fluid printing units reaching the outlet of the flow channel, which facilitates the spray of the fluid printing units in a single row. In particular, the size of the outlet of the flow channel is designed in such a structural form as to be 1.2 times the size of the fluid printing unit, which not only facilitates the spray of the fluid printing units in a single row, but also can avoid that the second material wraps the first material in an excessive thickness in the case of ensuring that the first material is not damaged, and facilitate further raising the flow rate of the fluid printing units at the outlet of the flow channel, and ensure a single-row and uniform spray of the fluid sprinting units.

Further, the inlet of the flow channel is sized to be n times the size of the fluid printing unit, wherein n=2-5. Preferably, the inlet of the flow channel is sized to be 2 times the size of the fluid printing unit.

In the improved technical solution, the size of the inlet of the flow channel is designed in such a structural form as to be multiple times the size of the fluid printing unit. A plurality of fluid printing units, preferably two fluid printing units, may enter side by side at the inlet of the flow channel.

Further, an open recess is provided on an end surface of the extension rod adjacent to the spray head. An outlet of the open recess communicates with the flow channel, and the spray head extends into the open recess. The open recess is tapered toward the flow channel, and a second material flow channel is formed between an outer wall of the spray head and the open recess, forming a chamber between the outlet of the spray head and the outlet of the open recess. The second material passing through the second material flow channel wraps a first material sprayed from the spray head in the chamber, so as to form a fluid printing unit.

In the improved technical solution, by providing a tapered open recess on an end face of the extension rod adjacent to the spray head, a second material flow channel is formed between an outer wall of the spray head and the open recess, and a chamber is formed between the outlet of the spray head and the outlet of the open recess. The second material passes through the second material flow channel to enter the chamber and wraps the first material sprayed from the spray head, so as to form a mixed fluid printing unit which flows within the open recess. The open recess which is favorable for the convergence of the mixed fluid, ensures a more stable flow direction of the mixed fluid within the chamber and avoids its diffusion in the second material flow channel.

Further, a gap between the outlet of the spray head and the open recess is smaller than the size of the fluid printing unit.

In the improved technical solution, the gap between the outlet of the spray head and the open recess is designed to be smaller than the size of the fluid printing unit, which prevents the fluid printing unit from flowing toward the second material flow channel, and ensures that the fluid printing unit within the chamber flows stably to the flow channel of the extension rod.

Further, the open recess has a conical section taken along a flow direction of the fluid printing unit.

In the improved technical solution, the open recess is further designed in a conical structural form, so that the second material can more uniformly wrap the first material. Moreover, the conical flow channel is easy to process.

Further, the bioprinter spray head assembly further comprises a thermal insulation member on an outer periphery of the extension rod.

In the improved technical solution, the thermal insulation member on the outer periphery of the extension rod can ensure that the fluid printing unit keeps a desired temperature in the flow channel and maintains the activity of the fluid printing unit.

Preferably, the flow channel is straight or curved.

In the preferred technical solution, the straight flow channel or the curved flow channel can both enable the fluid printing unit to reduce the influence of the mechanical force in the printing process, and provide options in various spray directions.

The present disclosure further provides a bioprinter, which comprises the aforementioned bioprinter spray head assembly.

In the basic technical solution, the bioprinter comprising the aforementioned bioprinter spray head assembly also presents the aforementioned advantageous technical effect.

Preferably, the bioprinter is a 3D bioprinter.

In the preferred technical solution, the bioprinter spray head assembly is especially suitable for a 3D bioprinter.

Accordingly, on the basis of the aforementioned technical solution, the present disclosure provides a bioprinter spray head assembly, which is configured such that a fluid print unit serving as a biological printing material is orientedly sprayed through the flow channel by providing an extension rod having an elongated flow channel adjacent to the outlet of the spray head. The elongated flow channel can sequence the fluid printing units and guide the fluid printing units to spray. Compared to the structure in the prior art where the bottom outlet is suddenly narrowed, the fluid printing unit is subjected to a more uniform pressure in the draining and spraying process, and easily maintains a favorable flow ability. The flow direction of the biological printing material is more stable, which relieves the condition of mutual crowd and compression between the fluid printing units, and reduces the damage of the fluid printing unit by the mechanical force in the printing process.

BRIEF DESCRIPTION OF THE DRAWINGS

The drawings described herein are used to provide a further understanding of the present disclosure and constitute a part of the present application. The illustrative embodiments of the present disclosure as well as the descriptions thereof, which are merely used for explaining the present disclosure, do not constitute improper definitions on the present disclosure. In the drawings:

FIG. 1 is a schematic view of the structure of the bioprinter spray head assembly of the present disclosure.

EMBODIMENTS

Next, the technical solution of the present disclosure is further described in detail by means of the drawings and embodiments.

The specific embodiments of the present disclosure are further described in order to facilitate understanding of the concept of the present disclosure, the technical problem to be solved, the technical features constituting the technical solution and the technical effect produced therefrom. It is necessary to explain that, the explanations for such embodiments do not constitute definitions on the present disclosure. In addition, the technical features involved in the embodiments of the present disclosure described below may be combined with each other as long as they do not constitute a conflict therebetween.

Considering that the existing bioprinter spray head assembly directly sprays the cells to a printing platform at the spray head, and a fluid as a printing material may be subjected to the damage caused by the mechanical force in the printing process, the present disclosure designs a bioprinter spray head assembly, which is configured such that a fluid print unit serving as a biological printing material is orientedly sprayed through the flow channel by providing an extension rod having an elongated flow channel adjacent to the outlet of the spray head. The flow channel can protect the fluid printing unit and reduce the damage of the fluid printing unit by the mechanical force in the printing process, so that it presents a high reliability.

In one illustrative embodiment of the bioprinter spray head assembly of the present disclosure, as shown in FIG. 1, the bioprinter spray head assembly comprises a spray head 1 and an extension rod 2 spaced from the spray head 1 and disposed adjacent to an outlet of the spray head 1, wherein an elongated flow channel 21 is provided in the extension rod 2 to guide a fluid printing unit serving as a biological printing material in the flow channel 21 to be orientedly sprayed.

In the illustrative embodiment, the extension rod 2 having a flow channel 21 may be disposed at a position adjacent to the outlet of the spray head 1 by means of a mounting block 3, and the fluid printing unit serving as a biological printing material is guided by the flow channel 21 such as to be orientedly sprayed. Compared to the structure in the prior art where the bottom outlet is suddenly narrowed, the fluid printing unit is subjected to a more uniform pressure in the draining and spraying process, and easily maintains a favorable flow ability. The flow direction of the biological printing material is more stable, which relieves the condition of mutual crowd and compression between the fluid printing units, and reduces the damage of the fluid printing unit by the mechanical force in the printing process.

The fluid printing unit refers to a printing unit of a biological printing material, which may be a unit composed of a single first material (for example bio-ink), and may also be a unit of mixed fluids consisting of a first material wrapped with a second material (for example hydrogel). In another embodiment, the extension rod 2 may also spray a strip-like continuous or non-continuous substance mixed with a fluid printing unit. At this time, the fluid printing unit may also be an elongated mixture, the overall structure of which is similar to sandwich noodles.

The flow channel 21 can perform an oriented sequence of the fluid printing unit, so as to reduce the possibility of clogging. For a fluid printing unit which is a mixed fluid printing unit formed by wrapping the first material with the second material, the flow channel 21 also facilitates the second material to uniformly wrap and protect the first material.

In addition, since the flow channel 21 which presents an elongated shape can prevent the damage produced by the friction between the biological printing material and the metal material in the printing process, the flow channel 21 can protect the fluid printing unit and reduce the influence of the damage of the fluid printing unit by the mechanical force in the printing process.

The flow channel 21 may be straight as shown in the drawing so that the fluid printing unit is sprayed downwards, and may also be arranged in a curved structural form according to the printing requirements, so as to provide more options in the spray direction.

As shown in FIG. 1, a thermal insulation member 22 may also be provided on the outer periphery of the extension rod 2. The thermal insulation member 22 can ensure that the fluid printing unit keeps a desired temperature in the flow channel 21 and maintains the activity of the fluid printing unit. As one embodiment, the thermal insulation member 22 is disposed lateral to a flow path of the fluid printing unit, and the thermal insulation member 22 is wrapped at a periphery along a movement path of the fluid printing unit, so as to achieve thermal insulation. Furthermore, such structural form overcomes the technical drawback that the spray head has to project certain length so as to facilitate applying a sprayed material in the case without an extension rod while thermal insulation is not available.

As an improvement to one aspect of the aforementioned embodiment, as shown in FIG. 1, the flow channel 21 is tapered from its inlet to outlet. The flow channel 21 is designed such that the fluid printing unit travels in the flow channel 21 to facilitate raising the flow rate of the fluid printing unit at the outlet of the flow channel 21 and reduce the possibility of its clogging. Preferably, the cross section of the flow channel 21 taken along the flow direction of the fluid printing unit is conical. The conical flow channel 21 in a structural form similar to a funnel or a subway gate makes a more uniform distribution of the fluid printing unit in the flow channel 21, and further reduces the possibility of its clogging. Moreover, the conical flow channel which is easy to process, presents a favorable implementability.

Specifically or preferably, on the one hand, the inlet of the flow channel 21 is sized to be n times the size of the fluid printing unit, wherein n=2-5. Within the preferable size range, the problem of clogging at the inlet of the flow channel 21 can be effectively avoided. Preferably, the inlet of the flow channel 21 is sized to be 2 times the size of the fluid printing unit so that the inlet of the flow channel 21 is only accessible for two fluid printing units side by side at most. Since the flow channel 21 is a tapered flow channel, it is only possible to flow out a single row of fluid printing units reaching the outlet of the flow channel 21, such as to enable further reducing the possibility of the clogging of the fluid printing unit, and facilitating the spray of the fluid printing units in a single row. It is necessary to explain that: the inlet of the flow channel 21 described in the present embodiment may be a circular hole channel, and thus the fluid printing unit recited in the present embodiment may be in the shape of a sphere. At this time, the size of the inlet of the flow channel 21 recited in the present embodiment is the diameter at the inlet of the flow channel 21, and the size of the fluid printing unit is the diameter of the fluid printing unit.

On the other hand, the outlet of the flow channel 21 is sized to be 1-1.5 times, preferably 1.2 times the size of the fluid printing unit. Within the size range, the flow channel 21 not only facilitates the spray of the fluid printing units in a single row, but also can avoid that the second material wraps the first material in an excessive thickness in the case of ensuring that the first material is not damaged, and facilitate further raising the flow rate of the fluid printing unit at the outlet of the flow channel, and ensuring the continuity and uniformity of the spray of the fluid printing unit in a single row.

As an improvement to another aspect of the aforementioned embodiment, as shown in FIG. 1, an open recess 23 is provided on an end surface of the extension rod 2 adjacent to the spray head 1. An outlet of the open recess 23 communicates with the flow channel 21, and the spray head 1 extends into the open recess 23. The cross section of the open recess 23 is tapered toward the flow channel 21, and a second material flow channel is formed between an outer wall of the spray head 1 and the open recess 23, forming a chamber between the outlet of the spray head 1 and the outlet of the open recess 23. The second material passing through the second material flow channel wraps a first material sprayed from the outlet of the spray head 1 in the chamber, so as to form a fluid printing unit. By providing a tapered open recess 23 on an end face of the extension rod 2 adjacent to the spray head 1, a second material flow channel is formed between an outer wall of the spray head 1 and the open recess 23, and a chamber is formed between the outlet of the spray head 1 and the outlet of the open recess 23. The second material passes through the second material flow channel to enter the chamber and wraps the first material sprayed from the spray head, so as to form a mixed fluid printing unit.

Among them, regarding the first material and the second material, one preferred embodiment is that, the first material is a printing material containing cells (for example bio-ink), and the second material is a printing material that does not contain cells. In this embodiment, more preferably, the second material is a material with temperature-sensitive properties, especially a biocompatible material with temperature-sensitive properties and certain viscosity (for example hydrogels). Certainly, as another embodiment, the first material is a printing material that does not contain cells, while the second material is a printing material that contains cells. In the remaining embodiments, the first material and the second material may also be printing materials that both contain cells, or may also be printing materials that do not contain cells.

Regarding the morphology of the first material and the second material, either or both of the first material and the second material are one of the following several morphologies: homogeneous, non-homogeneous (e.g., granular mixture), continuous or discontinuous fluid.

Specifically, since a second material flow channel is formed between the outer wall of the spray head 1 and the tapered open recess 23, the second material flow channel has the function of a uniform pressure. Even if the second material enters the second material flow channel from one side as shown in FIG. 1, it still presents a uniform pressure intensity within the second material flow channel, thereby ensuring that the biological material presents a uniform wrapping effect at one side adjacent to or far from the second material inlet. In the embodiment, the section of the open recess 23 taken along the flow direction of the fluid printing unit, is preferably conical, and the open recess 23 presenting a conical structure allows the second material to flow along a conical face of the open recess 23, which produces the effect of converging towards the outlet of the spray head 1, and facilitates the uniform wrapping of the first material unit by the second material unit. The open recess 23 of the structural form can also ensure a more stable flow direction within the chamber.

The mixed fluid printing unit flows within the open recess 23, and the open recess 23 facilitates the convergence of the fluid printing unit toward the flow channel 21 of the extension rod 2, so as to ensure that the flow direction of the mixed fluid printing unit within the chamber is more stable, and avoid its diffusion in the second material flow channel.

As shown in FIG. 1, there is a gap between the outlet of the spray head 1 and the open recess 23. Specifically or preferably, the gap between the outlet of the spray head 1 and the open recess 23 is smaller than the size of the fluid printing unit, which can prevent the fluid printing unit from reversely flowing toward the second material flow channel, and ensure that the fluid printing unit within the chamber flows stably to the flow channel 21.

In one embodiment of the bioprinter spray head assembly according to the present disclosure, the process of wrapping the first material with the second material is as follows:

The first material after being sprayed from the spray head 1, enters the chamber between the outlet of the spray head 1 and the outlet of the open recess 23. The second material enters the chamber through the second material flow channel formed between the outer wall of the spray head 1 and the open recess 23. The second material in the chamber has certain pressure, and the second material is compressed such as to be adhered to a portion of the first material unit projecting from the spray head 1. Until the entire first material unit is sprayed, the second material completely wraps the first material unit, to form a mixed fluid printing unit. At this time, a portion of the fluid printing unit has already entered the flow channel 21 of the extension rod 2. Finally, the first material unit enters the flow channel 21 of the extension rod 2 under the continuous wrapping of the second material, and the first material unit surrounded by the second material orientedly flows within the flow channel 21, and is uniformly wrapped, and sequentially sprayed.

In the flow process, the first material is adequately and uniformly wrapped by the second material, and the second material which is wrapped around the first material to form a protective structure before the first material is sprayed from the outlet of the flow channel 21, further reduces the influence of the printing process over the first material.

The present disclosure further provides a bioprinter, which comprises the aforementioned bioprinter spray head assembly. As the bioprinter spray head assembly of the present disclosure can prevent clogging of the biological printing material, the bioprinter according to the present disclosure also correspondingly has the advantageous technical effects described above. Especially, the bioprinter is a 3D bioprinter, and the bioprinter spray head assembly of the present disclosure is especially suitable for a 3D bioprinter.

The above-combined embodiments make detailed explanations for the embodiments of the present disclosure, but the present disclosure is not limited to the embodiments described. For example, the extension rod 2 may be integrated with the spray head 1 without needing to provide the mounting block 3. For a person skilled in the art, multiple changes, modifications, equivalent replacements, and variations made to such embodiments still fall within the protection scope of the present disclosure without departing from the principles and substantive spirit of the present disclosure.

What is claimed is:

1. A bioprinter spray head assembly, comprising a spray head and an extension rod spaced from the spray head and disposed adjacent to an outlet of the spray head, wherein an elongated flow channel is provided in the extension rod and the flow channel is configured to guide a fluid printing unit serving as a biological printing material in the flow channel to be orientedly sprayed, an open recess is provided on an end surface of the extension rod adjacent to the spray head, wherein an outlet of the open recess communicates with the flow channel, the spray head extends into the open recess which is tapered toward the flow channel a second material flow channel is formed between an outer wall of the spray head and the open recess, a chamber is formed between the outlet of the spray head and the outlet of the open recess, the chamber is configured to allow a second material passing through the second material flow channel to wrap a first material sprayed from the outlet of the spray head so as to form the fluid printing unit.

2. The bioprinter spray head assembly according to claim 1, wherein the flow channel is tapered from its inlet to outlet.

3. The bioprinter spray head assembly according to claim 2, wherein the flow channel has a conical section taken by along a flow direction of the fluid printing unit.

4. The bioprinter spray head assembly according to claim 2, wherein the outlet of the flow channel is sized to be 1-1.5 times the size of the fluid printing unit.

5. The bioprinter spray head assembly according to claim 4, wherein the outlet of the flow channel is sized to be 1.2 times the size of the fluid printing unit.

6. The bioprinter spray head assembly according to claim 2, wherein the inlet of the flow channel is sized to be 2-5 times the size of the fluid printing unit.

7. The bioprinter spray head assembly according to claim 6, wherein the inlet of the flow channel is sized to be 2 times the size of the fluid printing unit.

8. The bioprinter spray head assembly according to claim 1, wherein a gap between the outlet of the spray head and the open recess is smaller than the size of the fluid printing unit.

9. The bioprinter spray head assembly according to claim 1, wherein the open recess has a conical section taken by along a flow direction of the fluid printing unit.

10. The bioprinter spray head assembly according to claim 1, further comprising a thermal insulation member on an outer periphery of the extension rod, the thermal insulation member is configured to keep a temperature of the fluid printing unit in the flow channel.

11. The bioprinter spray head assembly according to claim 1, wherein the flow channel is straight or curved.

12. A bioprinter, comprising the bioprinter spray head assembly according to claim 1.

13. The bioprinter according to claim 12, wherein the bioprinter is a 3D bioprinter.

* * * * *